United States Patent [19]
deCroos et al.

[11] Patent Number: 5,696,241
[45] Date of Patent: Dec. 9, 1997

[54] SULFONATED QUINOLONE COMPOUND AND METHOD OF PREPARATION

[75] Inventors: Philomen Z. deCroos; Ronald P. Pedemonte, both of Coventry; Thomas S. Phillips, North Providence, all of R.I.

[73] Assignee: Dystar, L.P., Charlotte, N.C.

[21] Appl. No.: 784,935

[22] Filed: Jan. 15, 1997

[51] Int. Cl.$^6$ .................... C09B 62/006; C09B 62/085; C09B 62/51; C07D 215/227
[52] U.S. Cl. .................... 534/635; 534/642; 534/771; 546/155
[58] Field of Search .................... 534/635, 642, 534/771; 546/155

[56] References Cited

U.S. PATENT DOCUMENTS

| | | | |
|---|---|---|---|
| 1,893,646 | 1/1933 | Holzach et al. | 534/771 X |
| 2,231,705 | 2/1941 | Dickey | 546/155 X |
| 2,529,924 | 11/1950 | Dickey | 546/155 X |

FOREIGN PATENT DOCUMENTS

| | | | |
|---|---|---|---|
| 58-101171 | 6/1983 | Japan . | |
| 327380 | 4/1930 | United Kingdom | 534/771 |
| 441628 | 1/1936 | United Kingdom | 534/771 |
| 561054 | 5/1944 | United Kingdom | 534/771 |

OTHER PUBLICATIONS

Cipolli et al., Chemical Abstracts, 89:36856e (1982).
Stefaniak, Chemical Abstracts, 77:7281r (1972).
Sueda et al., Chemical Abstracts, 82:172594f (1975).
Hawley's Condensed Chemical Dictionary, 11th ed., sulfuric acid, fuming (oleum), p. 1108, 1987.

*Primary Examiner*—Fiona T. Powers
*Attorney, Agent, or Firm*—Scott E. Hanf

[57] ABSTRACT

Novel sulfonated quinolone compounds used in the preparation of fiber reactive dyes having the formula:

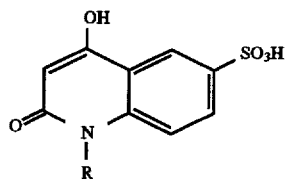

being N-alkyl substituted-4-hydroxy-6-sulfo-2-quinolone. The alkyl group bonded to the nitrogen in the quinolone has from 1 to 4 carbon atoms which may be further substituted by an hydroxy, amino, or sulfo group. The compounds of the invention may be prepared by the sulfonation of an N-alkyl substituted-4-hydroxy-2-quinolones,

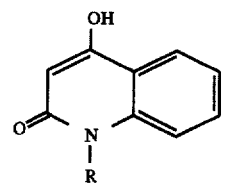

followed by selective desulfonation to yield the compounds of interest. New monoazo fiber reactive dyes having the formulas:

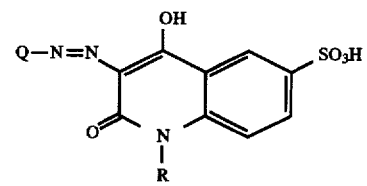

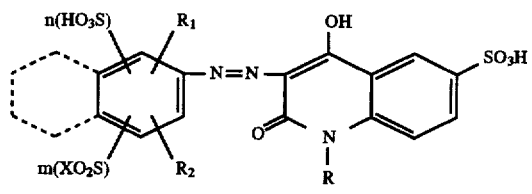

and

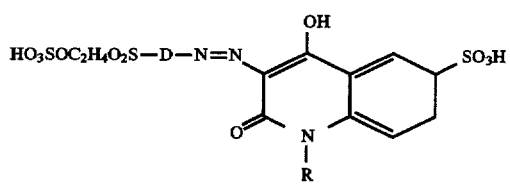

and their metal complexes, may be prepared from these sulfonated compounds by the diazotization of an amine component, selected from an unsubstituted, or a substituted benzene or naphthalene compound, containing a fiber reactive group, and coupling the diazo component to the compounds of the invention. These dyes are suitable for the dyeing and printing of native and synthetic carbonamide containing fibers, and native or regenerated or synthetic hydroxy containing fibers, especially on cellulose fibrous materials, in the presence of an alkaline agent.

15 Claims, No Drawings

SULFONATED QUINOLONE COMPOUND AND METHOD OF PREPARATION

FIELD OF THE INVENTION

The present invention is directed to sulfonated quinolone compounds and a method of preparation of the sulfonated quinolone compounds. The sulfonated quinolone compounds are useful in the preparation of fibers reactive dyes and as a component of fiber reactive dyes.

BACKGROUND OF THE INVENTION

Fiber reactive dyes form a chemical bond with the fiber being colored, and because of this are generally considered to possess excellent fastness properties. The largest class of fiber reactive dyes are those containing one or more azo groups (N=N). Fiber reactive dyes containing one azo group are referred to as monoazo fiber reactive dyes, those containing two azo groups as diazo fiber reactive, and so on. The fiber reactive azo dyes are generally prepared by the chemical reaction, between a diazo component and a coupling component, referred to as a coupling reaction. The fiber reactive dyes are useful for the dyeing and printing of cellulosic materials such as cotton, linen, rayon (e.g. viscose rayon) or staple fibers. They may also be used on wool, silk, or polyamide fibers.

The search is ongoing for new coupling components which are both useful and economical in the production of fiber reactive dyes.

SUMMARY OF THE INVENTION

The present invention is directed to sulfonated quinolone compounds and a method of preparation of the sulfonated quinolone compounds. The sulfonated quinolone compounds are useful in the preparation of fibers reactive dyes and as a component of fiber reactive dyes. More particularly, these sulfonated quinolones can be described as N-alkyl substituted-4-hydroxy-6-sulfo-2-quinolone, as shown in formula (1)

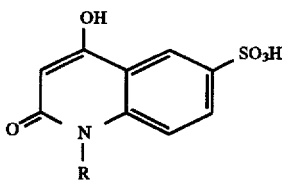
(1)

N-alkyl substituted, as used throughout this application shall mean either 1) an alkyl group having from 1 to 4 carbon atoms or 2) the foregoing alkyl group having from 1 to 4 carbon atoms, with one or more of said carbon atoms having one or more hydrogens substituted by a hydroxy group, an amino group, a sulfo group, or combinations thereof.

This invention also provides a process for preparing a sulfonated quinolone comprising the steps of providing an N-alkyl substituted-4-hydroxy-2-quinolone, as shown in formula (2)

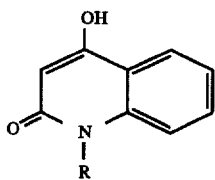
(2)

sulfonating the N-alkyl substituted-4-hydroxy-2-quinolone to produce a N-alkyl substituted-4-hydroxy-3,6-disulfo-2-quinolone as shown in formula (3)

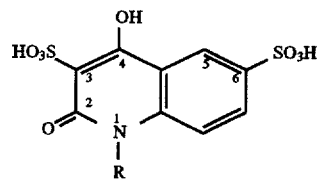
(3)

and selectively removing the sulfo group added to the number 3 position to yield a N-alkyl substituted-4-hydroxy-6-sulfo-2-quinolone as shown in formula (1).

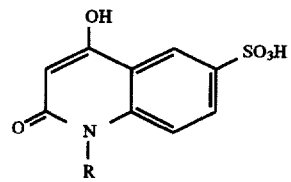
(1)

The sulfonated quinolone of the present invention can be used to prepare a fiber reactive dye as shown in formula (4)

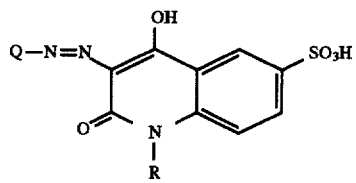
(4)

where Q is a diazo component.

DETAILED DESCRIPTION OF THE INVENTION

The present invention relates to a sulfonated quinolone compounds useful in the preparation of fiber reactive dyes. The compounds are of the general formula:

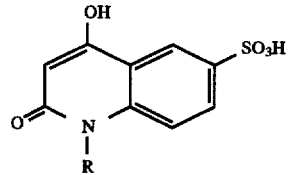
(1)

or N-alkyl substituted-4-hydroxy-6-sulfo-2-quinolone. The R in formula (1) is either 1) a $C_1$ to $C_4$ alkyl group or 2) a $C_1$ to $C_4$ alkyl group having one or more hydrogens substituted by a hydroxy group (OH), amino group ($NH_2$), or sulfo ($SO_3H$) group or a combination thereof. This sulfonated quinolone can be used effectively as a coupling agent for azo dyes predominantly in the yellow shade range.

These sulfonated quinolone compounds are prepared by a process of sulfonation and selective desulfonation. The first step of the process is to obtain an N-alkyl substituted-4-hydroxy-2-quinolone, as shown in formula (2)

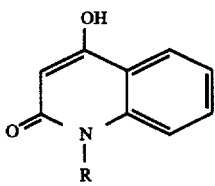

where R is defined above. An example of this class of compound is 1-methyl-4-hydroxy-2-quinolone which is commercially available from Pure Organics, India or Crystal Chem, India.

The N-alkyl substituted-4-hydroxy-2-quinolone is then sulfonated. Preferably sulfonation occurs in the presence of a sulfonating agent. An exemplary sulfonating agent is the mixture of sulfur trioxide and sulfuric acid. This mixture can be anywhere from a 5–65% by weight sulfur trioxide in concentrated sulfuric acid. Sulfonation can be carried out from 80° C. to 120° C. However, the preferred range for sulfonation is from 100° C. to 110° C. This sulfonation process results in selective addition of the sulfo group to the N-alkyl substituted-4-hydroxy-2-quinolone in the 3 and 6 position, as shown in formula (3).

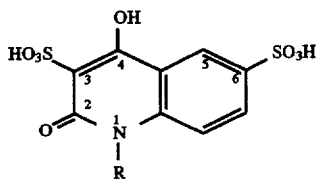

The next step of the process is to remove the sulfo group from position 3. This will be referred to as selective desulfonation. Selective desulfonation can be achieved by reacting the resulting product of an N-alkyl substituted-4-hydroxy-3,6-sulfo-2-quinolone with a desulfonating agent. An exemplary desulfonating agent is aqueous sulfuric acid. Concentration of the aqueous sulfuric acid used in this step range from 40 to 90% by weight, with the preferred range being from 60 to 75% by weight. Selective desulfonation can be carried out in the temperature range of 80° C. to 120° C. The preferred range being from 100° C. to 110° C.

The selectively desulfonated coupling agent, N-alkyl substituted-4-hydroxy-6-sulfo-2-quinolone shown in formula (1) can be used to prepare a fiber reactive dye as shown in formula (4)

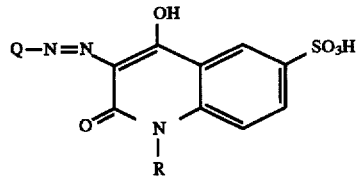

where Q (defined below) can be any diazo component.

One group of fiber reactive dyes can be further described as having the structure as shown in formula (5)

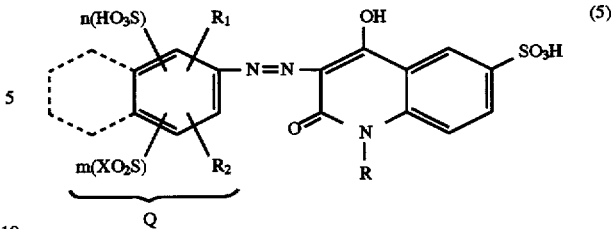

where X is the group —CH=CH$_2$ or —CH2—CH2—Z, with Z being a hydroxyl group or an inorganic or organic radical capable of being split off by the action of an alkaline reagent. R$_1$ and R$_2$, in this formula are independently selected from the group of C$_1$ to C$_4$ alkyl, C$_1$ to C$_4$ alkoxy, carboxy, hydroxy, chloro, bromo, fluoro, or an amino group which is further substituted by a nitrogen heterocyclic fiber reactive group of the series, 1,3,5 mono or dichloro triazinyl, 1,3,5 mono or difluoro triazinyl, trichloropyrimidinyl, difluoropyrimidinyl, or monochlorodifluoro pyrimidinyl, the nitrogen heterocycle may be further substituted by an alkyl or aryl amino compound containing the group SO$_2$-X, wherein X has the meaning as described above. n and m are integers (meaning 0, 1, or 2). The diazo component may be of the benzene or naphthylene series. The R group attached to the quinolone coupling agent has the same meaning as previously described.

The inventive coupling agent can also be used in the preparation of reactive dye compounds as shown in formula (6)

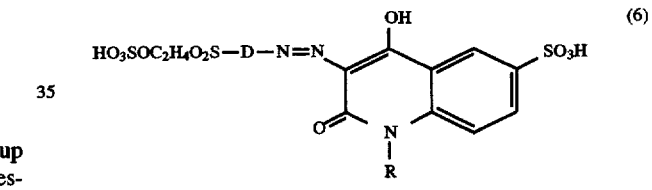

where D represents a phenyl or naphthyl ring, which may be substituted further by sulfo, carboxy, halogen, C 1–4 alkyl, or C 1–4 alkoxy group. In the quinolone coupling agent, off the nitrogen, in the 1 position is an R group, which has been previously described.

The monoazo dyes obtainable from the invention are very suitable for the dyeing and printing of various materials, for example, wool, silk, synthetic polyamide materials, and especially native or regenerated cellulose fibrous materials, for example, cotton, spun rayon and linen. They can advantageously be used in the dyeing and printing processes generally used in the industry for reactive dyes and yield, for example, on cellulose fibrous materials in the presence of alkaline agents dyeing with very good fastness properties.

EXAMPLES

The following examples illustrate the invention, the parts and percentages are by weight unless stated otherwise.

EXAMPLE 1

Into a 2 liter round bottom flask equipped with a mechanical stirrer, temperature probe, and drying tube were charged 1050 parts of 20% sulfur trioxide in sulfuric acid. 175 parts of 1-methyl-4-hydroxy-2-quinolone were then added allowing the temperature to rise to 100°–105° C. The reaction was stirred at 100°–105° C. until no starting material was detected. 250 parts of ice were added to the reaction, and stirring was continued at 100°–105° C. until the 3,6 desulfonated product was selectively desulfonated to yield only the 6-sulfo compound. The reaction was cooled to 25° C., and drowned onto 500 parts of ice, using an additional 500 parts of ice to maintain the temperature below 10° C. The slurry was filtered, and the resulting presscake was washed with 250 parts of ice water, and dried in an air oven at 60° C. to yield 253 parts of a dry powder having an assay of 95.3%.

EXAMPLE 2

Into a 1 liter beaker equipped with a mechanical stirrer, temperature probe, and pH probe were charged 100 parts of ice water, 15 parts of concentrated hydrochloric acid, and 28.1 parts of Aniline-4-[(2-sulfooxyethyl) sulfone]. 17.3 parts of a 40% aqueous solution of sodium nitrite was added and the reaction was stirred for two hours at 5°–10° C. 25.5 parts of 1-methyl-4-hydroxy-6-sulfo-quinolone were added, and the pH was adjusted to 5–6 by the addition of 13.5 parts of sodium carbonate. The solution was dried in an air oven at 60° C. to yield 76 parts of a yellow powder which dyed cellulose in a brilliant yellow shade.

EXAMPLE 3

Into a liter beaker equipped with a mechanical stirrer, temperature probe, and pH probe were changed 100 parts of ice water, and 31.1 parts of 2-methoxy-aniline-5-[(2-sulfooxyethyl)sulfone]. The pH was adjusted to 5.0–5.5 by the addition of 8.0 parts of sodium carbonate, and the solution was clarified over a filter aid. 25 parts of concentrated hydrochloric acid, and 100 parts of ice were added, followed by 17.6 parts of a 40% aqueous solution of sodium nitrite. The reaction was stirred for two hours at 5°–10° C. 25.5 parts of 1-methyl-4-hydroxy-6-sulfo-quinolone were added, and the pH was adjusted to 5–6 by the addition of 8.0 parts of sodium carbonate. The solution was dried in an air oven at 60° C. to yield 83 parts of a yellow powder which dyed cellulose in a brilliant yellow shade.

EXAMPLE 4

Into a 1 liter beaker equipped with a mechanical stirrer, temperature probe, and pH probe were charged 300 parts of water, and 50.0 parts of 2-methoxy-5-methyl-aniline-4-[(2-sulfooxyethyl) sulfone]. The pH was adjusted to 4.0–4.5 by the addition of 12.0 parts of sodium carbonate, 4 parts of activated charcoal were added, the solution stirred for one hour, and then clarified over a filter aid. 37.5 parts of concentrated hydrochloric acid, and 100 parts of ice were added, followed by 25.8 parts of a 40% aqueous solution of sodium nitrite. The reaction was stirred for two hours at 5°–10° C. 38.3 parts of 1-methyl-4-hydroxy-6-sulfo-quinolone were added, and the pH was adjusted to 5–6 by the addition of 12.0 parts of sodium carbonate. The solution was dried in an air oven at 60° C. to yield 101 parts of a yellow powder which dyed cellulose in a brilliant yellow shade.

EXAMPLE 5

Into a 1 liter beaker equipped with a mechanical stirrer, temperature probe, and pH probe were charged 300 parts of water, and 68.2 parts of 2,5-dimethoxy-aniline-4-[(2-sulfooxyethyl) sulfone]. The pH was adjusted to 5.0–5.5 by the addition of 16.0 parts of sodium carbonate, 4 parts of activated charcoal were added, the solution was stirred for one hour, and then clarified over a filter aid. 50.0 parts of concentrated hydrochloric acid, and 100 parts of ice were added followed by 34.8 parts of a 40% aqueous solution of sodium nitrite. The reaction was stirred for two hours at 5°–10° C. 38.3 parts of 1-methyl-4-hydroxy-6-sulfo-quinolone were added, and the pH was adjusted to 5–6 by the addition of 12.0 parts of sodium carbonate. The solution was dried in an air oven at 60° C. to yield 173 parts of an orange powder which dyed cellulose in a brilliant orange shade.

EXAMPLE 6

Into a 1 liter beaker equipped with a mechanical stirrer, temperature probe, and pH probe were charged 250 parts of ice water, and 52.0 parts of 1-sulfo-2-diazonaphthalene-6-[(2-sulfooxyethyl) sulfone]. 25.5 parts of 1-methyl-4-hydroxy-6-sulfoquinolone were added and the pH was adjusted to 5.0–5.5 by the addition of 10.0 parts of sodium carbonate. The solution was dried in an air oven at 60° C. to yield 115 parts of an yellow powder which dyed cellulose in a brilliant yellow shade.

EXAMPLE 7

Into a 1 liter beaker equipped with a mechanical stirrer, temperature probe, and pH probe were charged 100 parts of ice water, 20 parts of concentrated hydrochloric acid, and 29.7 parts of 2-aminophenol-5-[(2-sulfooxyethyl) sulfone]. 17.4 parts of a 40% aqueous solution of sodium nitrite were added, and the reaction was stirred for one hour. 25.5 parts of 1-methyl-4-hydroxy-6-sulfo-quinolone were added and the pH was adjusted to 7.0–7.5 by the addition of 15.0 parts of sodium carbonate. The reaction was stirred for 24 hours, then 25.0 parts of copper sulfate pentahydrate was added while maintaining the pH at 5.0–5.5 by the addition of 10 parts of sodium carbonate. The solution was dried in an air oven at 60° C. to yield 102 parts of a brown powder which dyed cellulose in a deep brown shade.

EXAMPLES 8–21

Further illustrative examples of the invention are shown in Table I, along with the shade of the fiber reactive dye produced.

TABLE I

| Ex | Diazo Component | Coupling Component | Shade |
|---|---|---|---|
| 8 | Aniline-4-[(2-sulfooxyethyl)sulfone]. | 1-methyl-4-hydroxy-6-sulfo-2-quinolone | yellow |
| 9 | 2-methoxy-aniline-5-[(2-sulfooxyethyl)sulfone]. | 1-methyl-4-hydroxy-6-sulfo-2-quinolone | yellow |
| 10 | 2-methoxy-5-methyl-aniline-4-[(2-sulfooxyethyl)sulfone] | 1-methyl-4-hydroxy-6-sulfo-2-quinolone | yellow |
| 11 | 2,5-dimethoxy-aniline-4-[(2-sulfooxyethyl)sulfone] | 1-methyl-4-hydroxy-6-sulfo-2-quinolone | orange |
| 12 | 1-sulfo-2-amino-naphthalene-6-[(2-sulfooxyethyl)sulfone] | 1-methyl-4-hydroxy-6-sulfo-2-quinolone | yellow |
| 13 | 2-aminophenol-5-[(2-sulfooxyethyl)sulfone]/Copper | 1-methyl-4-hydroxy-6-sulfo-2-quinolone | brown |

TABLE I-continued

| Ex | Diazo Component | Coupling Component | Shade |
|---|---|---|---|
| 14 | (structure: 2-amino-benzenesulfonic acid with SO₃H, NH₂, and NH linked to triazine bearing Cl and NH-phenyl-SO₂C₂H₄OSO₃H) | 1-methyl-4-hydroxy-6-sulfo-2-quinolone | yellow |
| 15 | (structure: benzene with SO₃H, HO₃S, NH₂, and NH linked to triazine bearing Cl and NH-phenyl-SO₂C₂H₄OSO₃H) | 1-methyl-4-hydroxy-6-sulfo-2-quinolone | yellow |
| 16 | (structure: 2-amino-benzenesulfonic acid with SO₃H, NH₂, and NH linked to triazine bearing NHCN and NH-phenyl-SO₂C₂H₄OSO₃H) | 1-methyl-4-hydroxy-6-sulfo-2-quinolone | yellow |
| 17 | (structure: 2-amino-benzenesulfonic acid with SO₃H, NH₂, and NH linked to difluoropyrimidine) | 1-methyl-4-hydroxy-6-sulfo-2-quinolone | yellow |
| 18 | (structure: benzene with SO₃H, HO₃S, NH₂, and NH linked to difluoropyrimidine) | 1-methyl-4-hydroxy-6-sulfo-2-quinolone | yellow |

TABLE I-continued

| Ex | Diazo Component | Coupling Component | Shade |
|---|---|---|---|
| 19 | ![structure] | 1-methyl-4-hydroxy-6-sulfo-2-quinolone | yellow |
| 20 | ![structure] | 1-methyl-4-hydroxy-6-sulfo-2-quinolone | yellow |
| 21 | ![structure] | 1-methyl-4-hydroxy-6-sulfo-2-quinolone | yellow |

The precise invention may be embodied in other specific forms and process without departing from the spirit or essential attributes thereof and, accordingly, reference should be made to the appended claims rather than to the foregoing specification, as indicating the scope of the invention.

What is claimed is:

1. A sulfonated quinolone having the formula

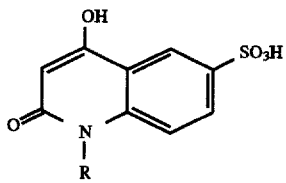

wherein R is an alkyl group having from one to four carbon atoms which is substituted with a group selected from hydroxy, amino, sulfo, or combinations thereof.

2. A process for preparing a sulfonated quinolone comprising the steps of:

providing an N-alkyl substituted-4-hydroxy-2-quinolone having the formula

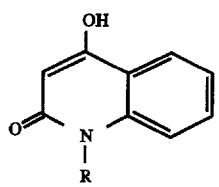

wherein R is an alkyl group having from one to four carbon atoms which is substituted with a group selected from hydroxdy, amino, sulfo or combinations thereof;

sulfonating said N-alkyl substituted-4-hydroxy-2-quinolone; and desulfonating selectively sulfo group added to the number 3 position.

3. The process of preparing the sulfonated quinolone according to claim 2 wherein sulfonation takes place in sulfur trioxide and sulfuric acid.

4. The process of preparing the sulfonated quinolone according to claim 2 wherein sulfonation of said N-alkyl substituted -4-hydroxy-2-quinolone occurs between 80° C. and 120° C.

5. The process of preparing the sulfonated quinolone according to claim 4 wherein sulfonation of said N-alkyl substituted-4-hydroxy-2 quinolone occurs between 100° C., and 110° C.

6. The process of preparing the sulfonated quinolone according to claim 2 wherein selective desulfonation takes places in aqueous sulfuric acid.

7. The process of preparing the sulfonated quinolone according to claim 6 wherein said desulfonating step occurs in aqueous sulfuric acid having a concentration of 40 to 90%.

8. The process of preparing the sulfonated quinolone according to claim 6 wherein said desulfonating step occurs in aqueous sulfuric acid having a concentration of 60 to 75%.

9. The process of preparing the sulfonated quinolone according to claim 2 wherein selective desulfonating of said N-alkyl substituted-4-hydroxy-2 quinolone occurs between 80° C. and 120° C.

10. The process of preparing the sulfonated quinolone according to claim 8 wherein selective desulfonation of said N-alkyl substituted-4-hydroxy-2 quinolone occurs between 100° C. and 110° C.

11. The process of preparing the sulfonated quinolone according to claim 3 wherein 5–65% sulfur trioxide is added to sulfuric acid.

12. A sulfonated quinolone having the formula

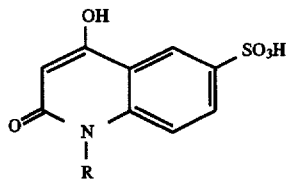

wherein R is an alkyl group having from one to four carbon atoms which substituted with a group selected from hydroxy, amino, sulfo or combinations thereof; and produced in accordance with the process of claim 2.

13. A fiber reactive dye having the general formula

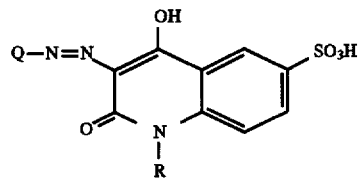

having a quinolone coupling agent wherein R is selected from the group consisting of 1) an alkyl group having from one to four carbon atoms or 2) the foregoing R substituted with a group selected from hydroxy, amino, sulfo, or combinations thereof; and having a diazo component Q.

14. The fiber reactive dye according to claim 13 of the general formula

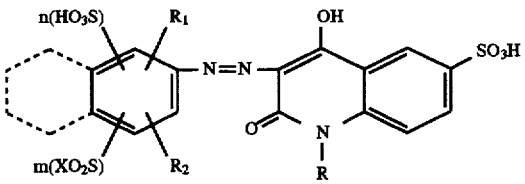

wherein the dotted line represents an optional fused benzene ring;

wherein X is selected from the group consisting of —CH=CH$_2$ or —CH2—CH2—Z;

wherein Z is selected from the group consisting of hydroxyl group, an inorganic radical or an organic radical;

said inorganic radical and said organic radical being capable of being split off by the action of an alkaline reagent;

wherein R$_1$ and R$_2$ are independently selected from the group consisting of a C$_1$–C$_4$ alkyl group a C$_1$–C$_4$ alkoxy group; carboxy; hydroxy; chloro; bromo; fluoro; or an amino group;

wherein said amino group is further substituted by the group consisting of a nitrogen heterocyclic fiber reactive group of the series 1, 3, 5 mono or dichloro triazinyl, 1, 3, 5 mono or difluoro triazinyl trichloropyrimidinyl, difluoropyrimidinyl, or monochlorodifluoro pyrimidinyl;

wherein said nitrogen heterocycle maybe substituted by a group consisting of an alkyl or aryl amino compound containing the group SO$_2$-X; and wherein n and m are integers.

15. A fiber reactive dye according to claim 13 of the formula

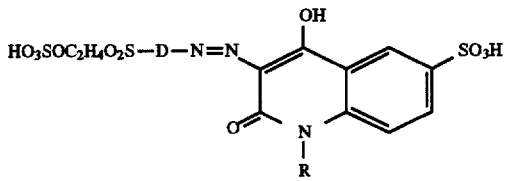

wherein D is selected from the group consisting of phenyl or naphthyl rings; and said phenyl and naphthyl rings may be substituted with a group selected from the group consisting of sulfo, carboxy, halogen, alkyl group having up to 4 carbons or an alkoxy group having up to 4 carbons.

* * * * *